United States Patent [19]

Shepherd

[11] Patent Number: 4,727,149
[45] Date of Patent: Feb. 23, 1988

[54] PREPARATION OF NITRILES OF FUSED RING PYRIDINE DERIVATIVES

[75] Inventor: Robin G. Shepherd, Maidenhead, England

[73] Assignee: John Wyeth & Brother Limited, Maidenhead, England

[21] Appl. No.: 776,335

[22] Filed: Sep. 16, 1985

Related U.S. Application Data

[63] Continuation-in-part of Ser. No. 472,787, Mar. 7, 1983, abandoned.

[30] Foreign Application Priority Data

Mar. 11, 1982 [GB] United Kingdom ............... 8207051

[51] Int. Cl.$^4$ ........................................... C07D 215/48
[52] U.S. Cl. ...................................... 546/176; 546/79; 546/93; 546/101; 546/104; 546/110; 546/112; 546/173; 546/177
[58] Field of Search ................... 546/79, 93, 101, 104, 546/110, 112, 173, 176, 177

[56] References Cited

U.S. PATENT DOCUMENTS

| | | | |
|---|---|---|---|
| 4,526,970 | 7/1985 | Shepherd | 546/104 X |
| 4,529,798 | 7/1985 | Shepherd | 546/104 X |
| 4,539,406 | 9/1985 | Crossley | 546/104 X |

FOREIGN PATENT DOCUMENTS

| | | |
|---|---|---|
| 1432378 | 4/1976 | United Kingdom . |
| 1458148 | 12/1976 | United Kingdom . |
| 1463668 | 2/1977 | United Kingdom . |
| 1471371 | 4/1977 | United Kingdom . |
| 1495993 | 12/1977 | United Kingdom . |
| 2088860A | 6/1982 | United Kingdom . |

OTHER PUBLICATIONS

Emmling et al., J. Org. Chem., vol. 24 (1959), p. 657.
Stowell et al., Synthesis, (1974), pp. 127–128.
Ruckdeschel et al., Pharmazie, vol. 31 (1976), p. 374.
Anderson et al, Can. J. Chem., vol. 49 (1971), p. 2315.
Levine et al., J. Org. Chem., vol. 39, (1974), p. 3556.
Lettre et al., Chem. Berichte, vol. 85, (1952), p. 397.

Primary Examiner—Donald G. Daus
Assistant Examiner—William A. Teoli, Jr.
Attorney, Agent, or Firm—George Tarnowski

[57] ABSTRACT

Nitriles of fused ring pyridine compounds such as 5,6,7,8-tetrahydroquinolines are prepared from metal derivatives of the starting compounds such as 8-litho-5,6,7,8-tetrahydroquinolines which have been prepared by treating a 5,6,7,8-tetrahydroquinoline with a metal amide prepared in situ from a metal alkyl and an N-benzylidine-N-alkylamine.

7 Claims, No Drawings

PREPARATION OF NITRILES OF FUSED RING PYRIDINE DERIVATIVES

This application is a continuation-in-part of our application U.S. Ser. No. 472,787 filed Mar. 7th 1983, now abandoned.

The invention relates to an improved method for preparing nitriles of fused ring pyridine compounds such as those described in UK Patent Application No. 1432378. The method is an improvement on that described in UK Patent Application No. 8135212 (Ser. No. 2088860A) and corresponding U.S. Pat. No. 4,529,798. The nitriles are anti-ulcer agents.

In UK Patent Application Serial No. 2088860A there is described a method for preparing nitriles and thioamides of fused ring pyridine compounds, such as 5,6,7,8-tetrahydroquinolines in which a metal derivative of the starting fused ring pyridine compound, such as an 8-lithio-5,6,7,8-tetrahydroquinoline, is treated with a dialkylcyanamide followed by treatment of the product with a proton source. The starting metal compound may be formed in situ by reaction of a 5,6,7,8-tetrahydroquinoline compound with a metal amide especially one derived from a hindered amine. We have now found that if the metal derivative of the tetrahydroquinoline is prepared using particular metal amides, which are conveniently prepared in situ in a particular way, then very good yields of the nitrile are obtained.

Accordingly the method of the invention comprises in one aspect a method of preparing nitriles of formula I

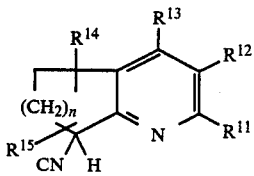

or acid addition salts thereof, wherein $R^{11}$, $R^{12}$, $R^{13}$, $R^{14}$ and $R^{15}$ are the same or different and represent hydrogen, alkyl of 1–6 carbon atoms, cycloalkyl of 4–6 carbon atoms, phenylalkyl of 7–12 carbon atoms or phenyl groups, any of which groups may be mono or disubstituted by alkyl of 1–6 carbon atoms, alkoxy of 1–6 carbon atoms, fluorine, trifluoromethyl, or $R^{11}$ and $R^{12}$ taken together, or $R^{12}$ and $R^{13}$ taken together, form a 5,6 or 7 membered saturated carbocyclic ring, $R^{14}$ and $R^{15}$ may also represent alkoxy of 1–6 carbon atoms, n is 1,2 or 3, in which a compound of formula II

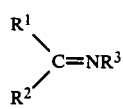

where $R^1$ is hydrogen, phenyl, phenyl substituted by alkyl of 1–6 carbon atoms, or a tertiary alkyl group of 4 to 6 carbon atoms; $R^2$ is phenyl, phenyl substituted by alkyl of 1–6 carbon atoms, or a tertiary alkyl group of 4 to 6 carbon atoms; $R^3$ is a branched chain alkyl of 3 to 6 carbon atoms; is reacted with a metal alkyl MR where R is an alkyl group of 2 to 6 carbon atoms, a phenyl group or phenyl substituted by alkyl of 1 to 6 carbon atoms, and M is lithium, sodium or potassium, in an inert non-polar solvent, to obtain a compound of formula III

wherein R, $R^1$, $R^2$, $R^3$ and M are as defined above, and this compound is treated with a compound of formula IV

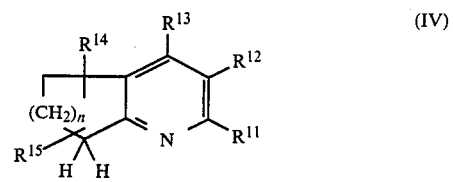

where $R^{11}$, $R^{12}$, $R^{13}$, $R^{14}$, $R^{15}$ and n are as defined in connection with formula I to obtain a compound of formula V

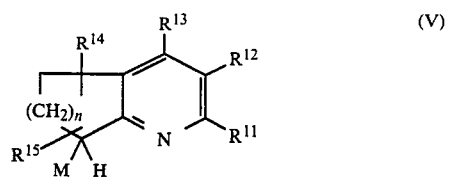

where M, $R^{11}$, $R^{12}$, $R^{13}$, $R^{14}$, $R^{15}$ and n are as defined above and the compound of formula V is treated with a compound of formula RaRbNCN wherein Ra and Rb are the same or different and represent alkyl of 1–6 carbon atoms, cycloalkyl of 4–6 carbon atoms or phenylalkyl of 7–12 carbon atoms, or Ra and Rb may be joined to form a 5,6 or 7 membered heterocyclic ring with the nitrogen atom to which they are attached and the product is treated with a proton source to obtain the nitrile of formula I.

The inert non-polar solvent for reaction of compound II with MR is preferably a hydrocarbon solvent such as benzene, toluene, xylene or hexane.

The reaction with the metal alkyl MR is preferably carried out at a temperature from −40° to +40° C. preferably about 0°–5° C.

Compound IV may be added to the reaction mixture in a hydrocarbon solvent as mentioned above or an ether solvent, e.g. ether, tetrahydrofuran or dioxan. The temperature may range from −70° C. to the reflux temperature of the solvent e.g. −20° C. to 80° C. When R11 and R12 are joined to form a ring the left and right hand rings are preferably of equal size and unsubstituted.

The proton source is preferably water e.g. in the form of an aqueous inorganic acid, e.g. hydrochloric, hydrobromic, sulphuric or nitric acid, or other aqueous medium, an alkanol e.g. of 1–6 carbon atoms, an organic acid, e.g. acetic acid, or ammonium chloride which can be added as a solid or in solution. When the proton source is an aqueous acid the product may be readily isolated in the form of an acid addition salt.

An alkyl group of 1–6 carbon atoms may be methyl, ethyl, n- or isopropyl, n-, s, t-butyl, pentyl or hexyl. An alkoxy group may be an alkyloxy group in which the alkyl portion is as defined for an alkyl group.

R³ may be isopropyl, s- and t-butyl or a branched chain pentyl or hexyl group. Preferably R³ is a tertiary alkyl radical such as t-butyl. R can be a primary, secondary or tertiary alkyl radical. Preferably the metal derivatives are the lithium compounds.

The acid addition salts include salts with inorganic acids e.g. hydrochloric, hydrobromic, sulphuric, or nitric acids or organic acids e.g. citric, fumaric, maleic or tartaric acids or organic sulphonic acids such as alkyl sulphonic acids e.g. methane sulphonic acid or aryl sulphonic acids e.g. p-toluene sulphonic acid.

The method of the present invention is especially useful when the compound of formula IV is a 5,6,7,8-tetrahydroquinoline containing a 4-alkyl substituent.

It is preferred to react the compound II with 2 mols of the metal alkyl to produce a mixture of the metal amide III and the metal alkyl and to react this in situ with the compound IV followed by the compound RaRbNCN. When R¹³ is alkyl or phenylalkyl containing a hydrogen atom on the carbon atom adjacent to the pyridine ring this procedure has considerable advantages as it gives higher yields of the compound I than when no metal amide is present during the reaction with RaRbNCN.

The preparation of the metal amides of formula III in situ from compounds II in the method of the present invention has advantages over their preparation from the corresponding amines.

The usual way of preparing such amines is by condensation of a ketone with a primary amine to prepare a ketimine which is then reduced. It has been reported [J. Organic Chem. 24, 657 (1959)] that methyl lithium can be reacted with N-benzylidene-t-butylamine in refluxing ether followed by treatment with water to give t-butyl(α-methylbenzyl)amine. However, the yield is only 20%. An improvement on the conventional route for preparing sterically hindered secondary amines, especially those containing t-butyl groups is described in Synthesis 1974, 127–8. This involves formation of the ketimine in the presence of titanium (IV) chloride and hydrogenation in situ. Yields of t-butyl secondary amines by this route are reported to range from 50–78%.

Pharmazie 31, H.6 (1976) pages 374–381 describes the preparation of various benzylamine derivatives and their investigation for anti-tubercular activity. This reference describes several routes to prepare these benzylamine derivatives including reaction of an N-alkylbenzylidinamine with a Grignard reagent or a lithium alkyl followed by hydrolysis and purification to give the desired amine. There is no mention in this reference of metal amide derivatives although it can be assumed that they would be formed.

In general it would be assumed from reading the above references that if a metal amide was desired for use in an organic reaction it would be necessary to first prepare it from the corresponding pure amine. The yields in the Pharmazie reference are variable so that even in the case of that reference it would be assumed that it would be necessary to first prepare the amine, isolate and purify it and then convert it to the metal derivative. However, we have found that the metal derivatives III prepared in situ from compounds II can be used in situ without purification to react with compound IV as the yields in this first stage are so high and the product is free from significant impurities.

The invention is illustrated by the following Examples:

EXAMPLE 1

Lithium N-t-butyl-N-(1-phenylpentyl)amide

A solution of N-benzylidine-t-butylamine (16.1g, 0.1M) in toluene (30 ml) was added to a mixture of a 1.55M solution of butyl lithium in hexane (64.5ml, 0.1M) and toluene (20 ml) at 0° C. under argon to form lithium N-t-butyl-N-(1-phenylpentyl)amide.

EXAMPLE 2

8-Cyano-4-methyl-5,6,7,8-tetrahydroquinoline

A solution of N-benzylidine-t-butylamine[1] (19.3g, 0.12M) in benzene (20 ml) was added to a solution of 1.55M butyl lithium in hexane (142 ml, 0.22M) maintained at 0° C under argon to form lithium N-t-butyl-N-(1-phenylpentyl)amide[2]. After 0.5 h. a solution of 4-methyl-5,6,7,8-tetrahydroquinoline (14.7g, 0.1M) in tetrahydrofuran (30 ml) was added. After a further 0.5 h. a solution of diisopropylcyanamide (14.0g, 0.11M) in tetrahydrofuran (30 ml) was added, the mixture stirred 0.5 h. then quenched with water(100 ml).

The aqueous phase was extracted with toluene. The combined organic extracts were washed with water, dried and evaporated. The residue crystallised on trituration with hexane to yield 14.1g (84%) of a crystalline mixture containing 95% of the title compound and 5% isomeric nitrile [(5,6,7,8-tetrahydro-4-quinolyl)-acetonitrile]3

The mixture is dissolved in methanol and treated with an excess of ethereal hydrogen chloride. Removal of the resulting crystals by filtration gives the title compound as the hydrochloride (12.7g, 76%) m.p. 253-5° C. identical with authentic material.

1. Reference: J. Organic Chem. 24 657 (1959)
2. At this point GLC indicates (after water quench) complete conversion N-t-butyl-N-(1-phenylpentyl)amine.
3. Can recover N-t-butyl-N-(1-phenylpentyl)amine by treating mother liquors with 5N hydrochloric acid and removing amine hydrochloride by filtration (ca 70% recovery), recovering to free base and distilling (Bp 100-4° C./5mbar).

The recovered amine can be used in the process described in UK Specification No. 2088860A to prepare more of the title compound. (Yields identical to above process).

I claim:

1. A method of preparing nitriles of formula I

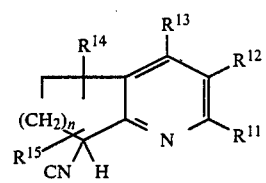

or acid addition salts thereof, wherein $R^{11}$, $R^{12}$, $R^{13}$, $R^{14}$ and $R^{15}$ are the same or different and represent hydrogen, alkyl of 1–6 carbon atoms, cycloalkyl of 4–6 carbon atoms, phenylalkyl of 7–12 carbon atoms or phenyl groups any of which groups may be mono or disubstituted by alkyl of 1–6 carbon atoms, alkoxy of 1–6 carbon atoms, fluorine or trifluoromethyl or $R^{11}$ and $R^{12}$ taken together, or $R^{12}$ and $R^{13}$ taken together, form a 5,6 or 7 membered saturated carbocyclic ring, $R^{14}$ and $R^{15}$ may also represent alkoxy of 1-6 carbon atoms, n is 1, 2 or 3, in which a compound of formula II

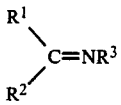
II where $R^1$ is hydrogen, phenyl, phenyl substituted by alkyl of 1-6 carbon atoms, or a tertiary alkyl group of 4 to 6 carbon atoms; $R^2$ is phenyl, phenyl substituted by alkyl of 1-6 carbon atoms or a tertiary alkyl group of 4-6 carbon atoms; $R^3$ is a branched chain alkyl of 3 to 6 carbon atoms; is reacted with a metal alkyl MR where R is an alkyl group of 2-6 carbon atoms, a phenyl or phenyl substituted by alkyl of 1-6 carbon atoms and M is lithium, sodium or potassium, in an inert non-polar solvent to obtain a compound of formula III

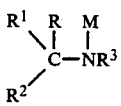
III wherein R, $R^1$, $R^2$, $R^3$ and M are as defined above, and this compound is treated with a compound of formula IV

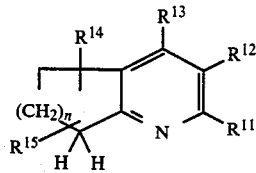
IV where $R^{11}$, $R^{12}$, $R^{13}$, $R^{14}$, $R^{15}$ and n are as defined in connection with formula I to obtain a compound of formula V

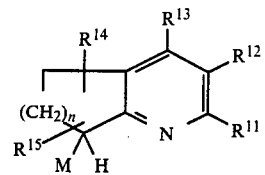
V where M, $R^{11}$, $R^{12}$, $R^{13}$, $R^{14}$, $R^{15}$ and n are as defined above and the compound of formula V is treated with a compound of formula RaRbNCN wherein Ra and Rb are the same or different and represent alkyl of 1-6 carbon atoms, cycloalkyl of 4-6 carbon atoms or phenylalkyl of 7-12 carbon atoms, or Ra and Rb may be joined to form a 5,6 or 7 membered saturated heterocyclic ring with the nitrogen atom to which they are attached and the product is treated with a proton source selected from water, an aqueous inorganic acid, an alkanol having 1-6 carbon atoms, an alkanoic acid having 1-6 carbon atoms or ammonium chloride to obtain the nitrile of formula I.

2. A method as claimed in claim 1, wherein the compound II is reacted with 2 mols of the metal alkyl MR per mol of compound II to produce a mixture of the metal amide III and the metal alkyl and this mixture is treated in situ with the compound IV followed by the compound RaRbNCN.

3. A method as claimed in claim 2, wherein a compound V is used and $R^{13}$ is alkyl or phenylalkyl containing a hydrogen atom on the carbon atom adjacent to the pyridine ring.

4. A method as claimed in claim 1, wherein the compound of formula IV is a tetrahydroquinoline in which n is 2.

5. A method as claimed in claim 1, wherein the compound of formula IV is 4-methyl-5,6,7,8-tetrahydroquinoline.

6. A method as claimed in claim 1, wherein the compound of formula II is one in which $R^1$ is hydrogen, $R^2$ is phenyl or phenyl substituted by alkyl and $R^3$ is t-butyl.

7. A method as claimed in claim 1, wherein the compound of formula II is N-benzylidine-t-butylamine.

* * * * *